US011717167B2

(12) United States Patent
Romfh et al.

(10) Patent No.: US 11,717,167 B2
(45) Date of Patent: Aug. 8, 2023

(54) IN-VIVO MONITORING OF CELLULAR ENERGETICS WITH RAMAN SPECTROSCOPY

(71) Applicants: John P. Romfh, Palo Alto, CA (US); Daryoosh Vakhshoori, Cambridge, MA (US); John N. Kheir, Charlestown, MA (US); Peili Chen, Andover, MA (US); Brian Polizzotti, Swampscott, MA (US); Joshua Salvin, Sherborn, MA (US); Alison Perry, Sevenoaks (GB)

(72) Inventors: John P. Romfh, Palo Alto, CA (US); Daryoosh Vakhshoori, Cambridge, MA (US); John N. Kheir, Charlestown, MA (US); Peili Chen, Andover, MA (US); Brian Polizzotti, Swampscott, MA (US); Joshua Salvin, Sherborn, MA (US); Alison Perry, Sevenoaks (GB)

(73) Assignees: Pendar Technologies, LLC, Cambridge, MA (US); Children's Medical Center Corporation, Boston, MA (US)

( * ) Notice: Subject to any disclaimer, the term of this patent is extended or adjusted under 35 U.S.C. 154(b) by 711 days.

(21) Appl. No.: 16/822,098

(22) Filed: Mar. 18, 2020

(65) Prior Publication Data
US 2020/0281474 A1    Sep. 10, 2020

Related U.S. Application Data

(63) Continuation of application No. PCT/US2018/051767, filed on Sep. 19, 2018.
(Continued)

(51) Int. Cl.
*A61B 5/00*    (2006.01)
*A61B 5/145*    (2006.01)
(Continued)

(52) U.S. Cl.
CPC .......... *A61B 5/0075* (2013.01); *A61B 5/1459* (2013.01); *A61B 5/14546* (2013.01);
(Continued)

(58) Field of Classification Search
CPC ...... G01N 21/65; A61B 5/0059; A61B 5/0075
See application file for complete search history.

(56) References Cited

U.S. PATENT DOCUMENTS

| | | |
|---|---|---|
| 7,113,814 B2 | 9/2006 | Ward et al. |
| 2004/0039269 A1 | 2/2004 | Ward et al. |

(Continued)

FOREIGN PATENT DOCUMENTS

| | | | |
|---|---|---|---|
| WO | 2009075768 A2 | 6/2009 | |
| WO | WO-2016126314 A1 * | 8/2016 | ........... A61B 5/0075 |

OTHER PUBLICATIONS

Pelletier, Michael J. "Quantitative analysis using Raman spectrometry." Applied spectroscopy 57.1 (2003): 20A-42A.*
(Continued)

*Primary Examiner* — Carolyn A Pehlke
(74) *Attorney, Agent, or Firm* — Smith Baluch LLP

(57) ABSTRACT

The inventors have developed tools for quantifying the mitochondrial redox state of in vivo, in situ tissue using resonance Raman spectroscopy. The tissue is illuminated with an excitation beam that causes the tissue to scatter Raman-shifted light, which is collected and analyzed to produce coefficients representing the relative concentrations of different chromophores in the tissue. These relative concentrations indicate the redox state of whole mitochondria, hemoglobin oxygen saturation, myoglobin oxygen saturation, and/or redox state of individual cytochrome complexes in mitochondria of the in vivo, in situ tissue. Quantifiable information about these states and/or saturations can be used to assess tissue health, including organ
(Continued)

(dys)function before, during, and after surgery. For example, this information can be used to predict impending cardiac failure, to guide surgical interventions, to monitor organ health after transplantation, or to guide post-operative care.

22 Claims, 13 Drawing Sheets

Related U.S. Application Data

(60) Provisional application No. 62/560,619, filed on Sep. 19, 2017.

(51) Int. Cl.
  *A61B 5/1459* (2006.01)
  *G01N 21/65* (2006.01)
  *A61B 5/1455* (2006.01)

(52) U.S. Cl.
  CPC ........ *A61B 5/14552* (2013.01); *A61B 5/7275* (2013.01); *G01N 21/65* (2013.01); *A61B 2505/05* (2013.01)

(56) References Cited

U.S. PATENT DOCUMENTS

2017/0000353 A1* 1/2017 Li .................... A61B 1/0615
2017/0202462 A1 7/2017 Motz et al.

OTHER PUBLICATIONS

Argade, Pramod V., Yuan-Chin Ching, and Denis L. RoussEAu. "Resonance Raman spectral isolation of the a and a3 chromophores in cytochrome oxidase." Biophysical journal 50.4 (1986): 613-620.*
Negrerie, Michel, et al. "Ultrafast heme dynamics in ferrous versus ferric cytochrome c studied by time-resolved resonance Raman and transient absorption spectroscopy." The Journal of Physical Chemistry B 110.25 (2006): 12766-12781.*
Thermo Scientific (Nicolet NXR spectrometer, www.hosmed.fi/wp-content/uploads/nxr9650-spec.pdf, 2007).*
Li, Ran, et al. "Effects of laser excitation wavelength and optical mode on Raman spectra of human fresh colon, pancreas, and prostate tissues." Journal of Raman Spectroscopy 45.9 (2014): 773-780.*
Hutsebaut, Didier, Peter Vandenabeele, and Luc Moens. "Evaluation of an accurate calibration and spectral standardization procedure for Raman spectroscopy." Analyst 130.8 (2005): 1204-1214.*
UVA Health (www.uvahealth.com/services/plastic-surgery/skin-graft; retrieved Nov. 29, 2022).*
BWTek (Spectral Resolution, www.bwtek.com/spectrometer-part-5-spectral-resolution/, retrieved Nov. 29, 2022).*
Edinburgh Instruments (Raman spectroscopy, www.edinst.com/blog/what-is-raman-spectroscopy/, retrieved Nov. 29, 2022).*
Zhang, Zhi-Min, Shan Chen, and Yi-Zeng Liang. "Baseline correction using adaptive iteratively reweighted penalized least squares." Analyst 135.5 (2010): 1138-1146.*
Brazhe, Nadezda A., et al. "In situ Raman study of redox state changes of mitochondrial cytochromes in a perfused rat heart." PLoS One 8.8 (2013): e70488.*
International Search Report and Written Opinion in International Patent Application No. PCT/US2018/051767 dated Jan. 24, 2019, 14 pages.

* cited by examiner

B. Mitochondrial spectrum

C. Myoglobin spectrum

D. Hemoglobin spectrum $$\text{Saturation of } S_2 = \frac{k_2 \cdot f_2}{k_1 \cdot f_1 + k_1 \cdot f_2}$$

If the height of library peak $S_1$ is twice the height of peak $S_2$ then the enhancement factor $f_1 = \frac{1}{2}$ and $f_2 = 1$. Thus, in the case of 50% saturation, $S_1$ will be twice the height of $S_2$ (e.g. $k_1 = 2$ and $k_2 = 1$).

e.g. $\dfrac{1 \cdot 1}{2 \cdot \frac{1}{2} + 1 \cdot 1} = 0.5$ or 50%

IN-VIVO MONITORING OF CELLULAR ENERGETICS WITH RAMAN SPECTROSCOPY

CROSS-REFERENCE TO RELATED APPLICATION(S)

This application is a bypass continuation of International Application No. PCT/US2018/051767, filed on Sep. 19, 2018, and entitled "In-Vivo Monitoring of Cellular Energetics with Raman Spectroscopy," which in turn claims priority, under 35 U.S.C. § 119(e), to U.S. Application No. 62/560,619, filed on Sep. 19, 2017, and entitled "In-vivo monitoring of cellular energetics with Raman spectroscopy." Each of these applications is incorporated herein by reference in its entirety.

FIELD

The present technology generally relates to critical care medicine and surgery, including ischemia and reperfusion of tissues in the perioperative period.

BACKGROUND

The adequate delivery of oxygen to mitochondria is vital to organ function. Abnormalities in oxygen delivery ($DO_2$) are central to the pathology of many critical illness states, including sepsis, shock, and the systemic inflammatory response syndrome. Deficient $DO_2$ not only leads to deficient energy production and may also lead to the formation of reactive oxygen species and establish the milieu for cellular injury and death. Currently, the adequacy of $DO_2$ is assessed using the oxyhemoglobin saturation of venous blood ($S_vO_2$). However, this measure provides only global information and may be falsely reassuring in the sickest patients. For example, patients with tissue edema, altered erythrocyte rheology, or microvascular arteriovenous shunting may experience impaired mitochondrial oxygen delivery yet have a normal or even elevated $S_vO_2$. Further, in some situations, understanding local oxygen delivery is desirable, as following vascular reconstruction or congenital heart surgery.

Oxygen is used within the mitochondrion to produce energy via aerobic metabolism. It serves as the final electron acceptor at complex IV of the electron transport chain (ETC) where electrons at higher energy potential originating from NADH and $FADH_2$ successively lose energy and are eventually transferred to oxygen. This energy loss drives proton pumps in complexes I, III, and IV to establish a membrane potential for use in ATP production. When oxygen delivery to the mitochondrion decreases below a critical level, the flux of electrons is diminished, causing significant upstream effects. One effect is that the concentration of proximal reducing agents (e.g., NADH) increases. Using its potent fluorescent properties, [NADH] has been used to visualize areas of compromised tissue oxygenation in real time using animal models of coronary ischemia and of cranial stimulation. Unfortunately, the presence of hemoglobin interferes with NADH fluorescence measurements, which has reduced the clinical utility of this tool.

Alternatively, deficient oxygen delivery may be quantified through assessment of mitochondrial redox state. It has long been recognized that the redox state of the active sites of electron flux within the ETC—mitochondrial cytochromes—is spectroscopically quantifiable and varies based on the availability of oxygen; deficient oxygen delivery results in the progressive reduction of cytochromes. Cytochrome a,a3 in complex IV is an ideal target for quantifying oxygen supply-demand relationships because it is oxidized directly by molecular dioxygen and accounts for >95% of cellular oxygen utilization. In the past, several groups have attempted to quantify the redox status of cytochrome a,a3 using absorbance spectroscopy. However, these efforts have been limited by the overlap in the absorption spectra of the cytochromes of interest and other heme moieties that are present in vivo (e.g., hemoglobin and myoglobin). This causes absorbance-based estimates of cytochrome redox status to vary artificially with changes in blood pressure and intravascular blood volume. Further, tissue edema and inhomogeneous tissue scattering complicate the determination of absolute concentrations of cytochrome components. More recently, refinements to this technique have permitted isolation of the cytochrome and hemoglobin signals, although these approaches are still limited to describing trends, rather than absolute values, of cytochrome redox status.

An alternative approach to the quantification of mitochondrial redox status is Raman spectroscopy, in which the wavelength of light from a narrow band laser is shifted to lower energy by a precise quantity determined by the frequency of the vibrational modes of the molecules encountered by the light. The wavelength shift (i.e., Stokes shift) of inelastically scattered light can be separated from fluorescence to measure a redox state-specific spectral signature of a molecule. In the special case of resonance Raman spectroscopy (RRS), the optically excited state overlaps a strong electronic absorption line, resulting in orders of magnitude enhancement of the Raman cross-section. Relevant to cellular energetics, the resonance Raman profiles of porphyrin structures (present in hemoglobin, myoglobin, and mitochondrial cytochromes) have been well described, and are amplified by 4-6 orders of magnitude (enhancement factor) when excited near the Soret absorption band (400-450 nm). This enhancement makes the in vivo quantification of small quantities of such structures possible, even in a complex environment. Using this approach, the redox state of mitochondrial cytochromes have been described in isolated mitochondria, in myocytes, and in bloodless tissues. The technique has also been applied to the measurement of tissue oxyhemoglobin saturation in vivo. Quantification of mitochondrial redox state in vivo may represent a powerful and specific predictor of impending cardiac failure.

SUMMARY

Traditional analysis of Raman spectra for detection of biological chromophores has relied on assignment of individual peaks in the spectrum to particular states of the chromophores. An improved approach is to use a spectral library comprising a broad Raman spectrum for each chromophore and to use a regression process to determine a weighted mathematical sum of all spectra in the library that (best) describes the measured spectra. For example, a library can be created of the heme-containing components found in myocardium, including isolated hemoglobin, myoglobin, and mitochondrial cytochromes, each in the oxidized/oxygenated and reduced/deoxygenated state (six components total). The fluorescence signals are removed from the collected and filtered raw spectrum, creating a refined estimate of the final resonance Raman (RR) spectrum. The relative concentration of each component is determined by calculating the regression coefficient of each in an equation explaining the final RR spectrum as a weighted sum of each component's spectrum. This allows calculation of oxyhemoglobin saturation ($S_{Hb}O_2$), oxymyoglobin saturation ($S_{Mb}O_2$), and the ratio of reduced to total mitochondrial cytochromes.

The present technology includes methods, profiles, medical measurement devices, and other products for accurate measurement of the adequacy of oxygen delivery and utilization at the mitochondrial level and the prediction of organ dysfunction or failure based on the redox state of the mitochondria. The inventive technology offers several advantages and improvements over previous Raman spectroscopy techniques for measuring tissue health. These advantages and improvements include: (1) quantification of the redox state of whole mitochondria (multiple cytochromes) rather than an individual cytochrome; (2) prediction of impending organ failure based on a threshold redox state value; (3) use of a myoglobin signal as an index to compare concentrations of other chromophores (e.g., mitochondrial signal over myoglobin signal should be a constant across animals while just the mitochondrial signal strength may vary based on the measurement conditions or tissue location); and (4) greater accuracy, particularly for resolving closely related chromophores.

The present technology uses the simultaneous measurement of all cytochromes in the mitochondria in order to quantify an overall mitochondrial redox state which accounts for the weighted average redox state of individual cytochromes in a combined measurement.

In addition to the advantages of accurate redox state quantification for the mitochondria, the present technology provides a practical, real-time, in-vivo approach for predicting impending organ failure based on a threshold value that has been experimentally determined. The predictive value of the measurement allows time for clinical intervention before organ failure occurs.

With Raman spectroscopy, according to the present technology, the organ's condition is determined based on the oxygen saturation state of hemoglobin or myoglobin or the redox state of the mitochondria. Such high-accuracy measurement is achieved with Raman spectroscopy (such as resonance Raman spectroscopy) interrogation of tissue, e.g., in a minimally invasive fashion. With methods and products according to the present technology, advantageously preclinical (ultra-early) states of organ ischemia, organ injury, and organ failure can be detected, severity can be determined, and the effectiveness of various treatments aimed at resolving the dysfunctional state can be determined, and other beneficial effects for patient care can be achieved. An organ can also be monitored during an induced ischemic state, such as during cardiopulmonary bypass or during transplant surgery, in order to assess the tissue state and viability upon reperfusion.

In order to accomplish these and other objects of the invention, the present technology in a preferred embodiment provides a tissue analysis method, comprising interrogating a biological material (such as an organ) with RRS to obtain spectroscopy results.

In another preferred embodiment, the present technology provides a method of predicting organ failure or mitochondrial dysfunction, comprising collecting Raman spectra from the tissue and using a regression library to quantify the relative concentrations of various molecules using a library of Raman spectra of the molecules in known states.

A further preferred embodiment provides a process for analyzing the spectroscopy results using a pre-established Raman spectroscopy library for target molecules in oxidized and reduced states and regression for determining the relative concentration of each molecule in the measured spectrum.

Another preferred embodiment of the present technology provides a medical measurement device comprising: a laser excitation source, a spectrometer for resonance Raman spectroscopy; and a biological probe optically connected to the spectrometer.

A further preferred embodiment of the present technology provides a computer system comprising a non-volatile memory to store a database of stored baseline Raman spectroscopy spectra and patient Raman spectra. The computer system includes a processor, storage (memory), and a (custom) user interface. In operation, the processor executes processes for analyzing the spectra according to instructions stored in the memory.

Yet another embodiment of the present technology includes a method of monitoring a patient. This method comprises measuring a resonance Raman spectrum of in vivo, in situ tissue of the patient with a Raman spectroscopy system and quantifying a mitochondrial redox state of the in vivo, in situ tissue based on the Raman spectrum.

Quantifying the mitochondrial redox state may include determining relative concentrations of a plurality of chromophores in the tissue based on a fit of the Raman spectrum to a reference Raman spectrum for each chromophore in the plurality of chromophores. This fit can be determined by performing a regression analysis. Quantifying the mitochondrial redox state may also comprise determining a redox state of whole mitochondria, a hemoglobin oxygen saturation, a myoglobin oxygen saturation, or a redox state of individual cytochrome complexes in mitochondria of the in vivo, in situ tissue.

Examples of this method may also include determining an organ dysfunction of the patient based on the mitochondrial redox state of the in vivo, in situ tissue. If the in vivo, in situ tissue comprises heart tissue, the organ dysfunction can include cardiac dysfunction or cardiac arrest. Alternatively, or in addition, the method may include predicting at least one of organ dysfunction of the patient or organ rejection by the patient based on the mitochondrial redox state of the in vivo, in situ tissue.

Measuring the Raman spectrum can occur during surgery on the in vivo, in situ tissue, in which case the method may further include determining adequacy of tissue protection during surgery based on the mitochondrial redox state of the in vivo, in situ tissue and/or predicting tissue function following reperfusion of the in vivo, in situ tissue based on the mitochondrial redox state of the in vivo, in situ tissue.

If the in vivo, in situ tissue comprises myocardial tissue, measuring the Raman spectrum can occur during and after cardiac bypass. If the in vivo, in situ tissue comprises coronary tissue, measuring the Raman spectrum can occur during bypass surgery. And if the in vivo, in situ tissue comprises organ tissue, measuring the Raman spectrum can occur during organ transplant surgery. The in vivo, in situ tissue can also include a skin graft or a skin flap.

Another embodiment of the present technology includes a system for monitoring a patient. This system includes a laser, a probe in optical communication with the laser, a spectrometer in optical communication with the probe, and a processor operably coupled to the spectrometer. In operation, the laser generates an excitation beam. The probe illuminates in vivo, in situ tissue of the patient with the excitation beam and collects a Raman signal emitted by the in vivo, in situ tissue in response to the excitation signal. The spectrometer generates a Raman spectrum from the Raman signal, and the processor quantifies a mitochondrial redox state of the in vivo, in situ tissue based on the Raman spectrum. The laser may be a single-mode laser configured to emit the excitation beam at a wavelength of 441 nm and a power of about 4 mW. And the spectrometer can have a Full Width at Half Maximum (FWHM) resolution of 8 $cm^{-1}$ and an absolute Stokes shift accuracy of <0.4 $cm^{-1}$.

Yet another embodiment includes a method of monitoring a patent. This method includes illuminating in vivo, in situ tissue of the patient with an excitation beam at a wavelength of 441 nanometers and collecting Raman-shifted light scattered from the in vivo, in situ tissue of the patient in response to the excitation beam. A spectrometer or other device determines a spectrum of the Raman-shifted light. A processor or other device determines relative concentrations of each of plurality of chromophores in the in vivo, in situ tissue based on the spectrum of the Raman-shifted light. A redox state of whole mitochondria, hemoglobin oxygen saturation, myoglobin oxygen saturation, or redox state of individual cytochrome complexes in mitochondria of the in vivo, in situ tissue is determined from the spectrum of the Raman-shifted light. This determination is used to determine and/or predict a dysfunction of the in vivo, in situ tissue.

In some cases, illuminating the in vivo, in situ tissue occurs during surgery. These cases may further comprise determining adequacy of tissue protection during surgery based on the at least one of the redox state of whole mitochondria, hemoglobin oxygen saturation, myoglobin oxygen saturation, or redox state of individual cytochrome complexes in mitochondria of the in vivo, in situ tissue.

Determining the relative concentrations of each of the plurality of chromophores may comprise determining an estimate of weighted spectra to the Raman spectrum, iteratively adjusting the estimate of weighted spectra, and determining the relative concentrations based on the estimate of weighted spectra.

The method may also include predicting tissue function following reperfusion of the in vivo, in situ tissue based on the at least one of the redox state of whole mitochondria, hemoglobin oxygen saturation, myoglobin oxygen saturation, or redox state of individual cytochrome complexes in mitochondria of the in vivo, in situ tissue.

Features of these embodiments can be interchanged, mixed, and matched to the extent that they are compatible with each other. For instance, the systems disclosed herein can be used to carry out the disclosed methods. And steps for the disclosed methods can be combined and/or repeated as desired.

BRIEF DESCRIPTIONS OF THE DRAWINGS

DETAILED DESCRIPTION

The present includes technology methods and products in which resonance Raman spectroscopy (RRS) interrogates biological material (such as an organ). Data from interrogating tissue may be used to detect preclinical (ultra-early) states of organ failure and other tissue dysfunction and disease states, determine severity of the organ failure or tissue dysfunction, and determine the effectiveness of various treatments aimed at resolving the organ failure or tissue dysfunction in a patient.

In order to accomplish these and other objects, the present technology in a preferred embodiment provides a tissue analysis method, comprising interrogating a biological material (such as an organ) with RRS to obtain spectroscopy results. The RRS used in the present technology is based on the Raman effect, which has been known for over 70 years and is caused by absorption of light leading to the transition of a molecule from the ground state to an excited state, followed by the emission of light with a different wavelength. The Raman effect has only recently, through the advancements and miniaturization of fiber optic, laser, and detector technology, become a practical technique for clinical use. Because each molecular species has its own characteristic molecular vibrations, a Raman spectrum provides a unique "fingerprint" useful for sample or marker identification.

Figure 1:
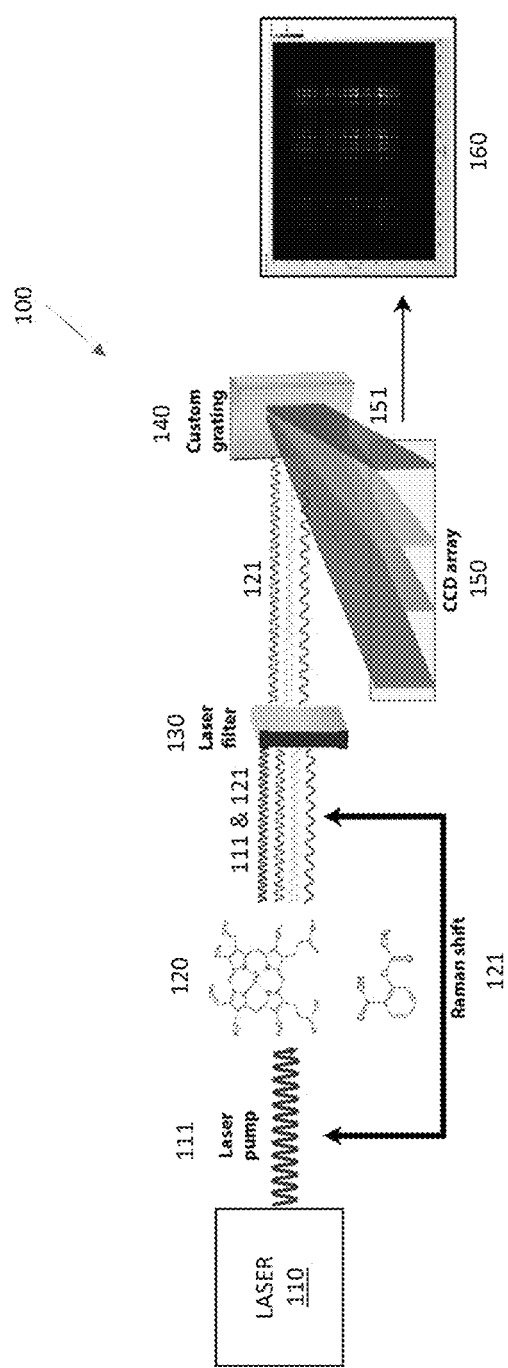
FIG. 1 is a schematic of a Raman spectroscopy system (spectrometer).

FIG. 1 shows a typical Resonance Raman spectrometer in which a laser pump source 111 is inelastically scattered from a target molecule 120 at a wavelength shifted from the pump source 121. A spectrometer comprising a filter 130 to remove the pump source light, a grating 140 to separate the light into its spectral components, and a detector, such as a CCD array 150, to collect the separated light, can be used to capture a spectrum 160 of the shifted light.

While any wavelength of light theoretically can be used as an excitation source to provide a Raman spectrum, visible excitation can produce strong broadband fluorescence, which undesirably can overwhelm Raman signals, which tend to be relatively weak. Nevertheless, wavelengths can be chosen that produce resonance due to matching of the excitation wavelength and the electronic energy state of the scattering molecule. While Raman scattering is a rather low energy phenomenon requiring sensitive detectors, the signal is greatly enhanced when the molecule of interest is resonant (absorption maximum near the laser wavelength). This signal enhancement at a resonant frequency may be referred to as "resonance Raman spectroscopy" (RRS) and allows for the selective detection of individual species of very low concentration within a complex mixture.

If the excitation wavelength does not induce fluorescence within the wavelength region of interest, then remarkably high-resolution Raman spectra can be obtained. If fluorescence occurs, it can be reduced or even eliminated in many instances by tuning the excitation wavelength. Alternatively, the slowly varying fluorescence can be removed from the sharp peaks of the Raman signal. In the present technology, the wavelengths for the Raman spectroscopy and/or fluorescence spectroscopy are wavelengths for which such spectroscopy equipment may be set, suitably for interrogating biological tissue in a living patient. Preferably resonance Raman spectroscopy according to the present technology is performed at an ultraviolet wavelength, i.e., at 390 to 460 nm. Modifications of Raman spectroscopy that can be applied include Fourier Transform Raman Spectroscopy, Nonlinear Raman Spectroscopy, Raman difference spectroscopy, and Raman Optical Activity.

The inventive methods, products, and profiles may include signal enhancement at a resonant frequency for a target molecule of the target molecule population. The inventive methods may include operating an electromagnetic radiation generator, such as a laser, at a range of selectable wavelengths from about 270 nm to about 20,000 nm. Spectroscopy may be performed for multiple wavelengths. Preferably the Raman spectroscopy is resonance Raman spectroscopy at 390 to 460 nm wavelength. Because basic Raman scattering is a rather low intensity phenomenon typically detected with sensitive detectors, preferably Resonance Raman Spectroscopy (RRS) techniques are used to enhance the signal when the molecule of interest is resonant (absorption maximum near the laser wavelength). The signal strength of Raman can be boosted by several orders of magnitude by providing areas of resonance. Also, use of resonant wavelengths allows limiting or reducing laser power density to levels well below the skin damage threshold of 4 watts/cm$^2$. Use of near UV wavelengths (e.g., blue light, ~441 nm) avoids the mutagenic potential of UV radiation, while ensuring a strong Raman signal.

Raman spectroscopy can be performed at many different individual wavelengths, but the resonant enhancement will change as a function of wavelength. For instance, the highest resonant enhancement occurs with excitation light near a Soret-absorption band. A wavelength of 441 nm is close to this band—and hence close to the highest enhancement—for the lowest concentration chromophore, in this case the mitochondrial cytochromes, cytochrome c oxidase (aa3). Other wavelengths could also be used, however. Additionally, it is possible to take separate scans at several discrete wavelengths emitted by a tunable laser or an array of lasers and combine the results in processing in order to better optimize multiple chromophores.

Figure 2A:
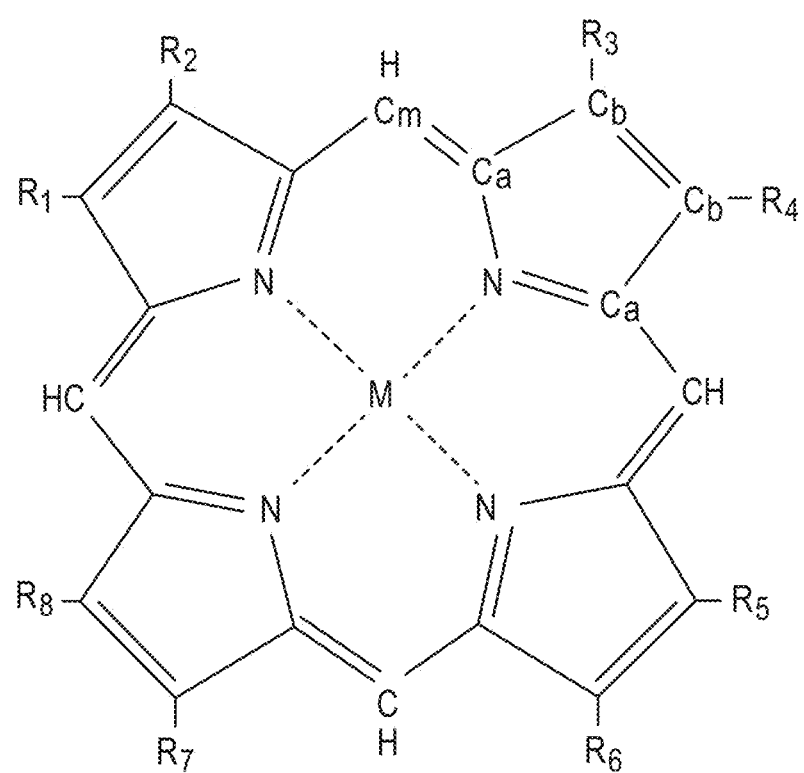
FIG. 2A is a schematic of a porphyrin ring.
Figure 2B:
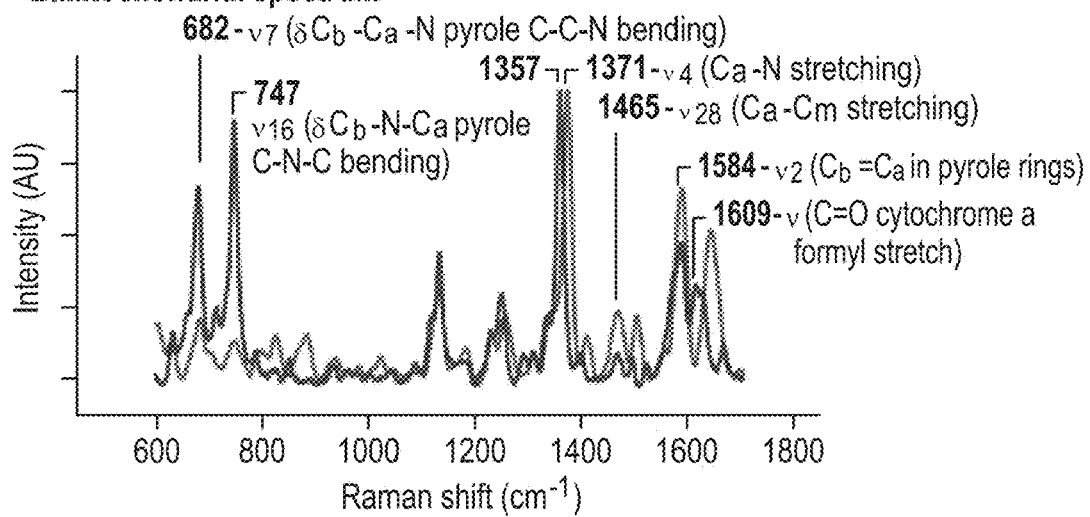
FIG. 2B is a plot of a mitochondrial spectrum created using a Raman spectrometer. The peak locations and vibrational mode assignments are known in the scientific literature.
Figure 2C:
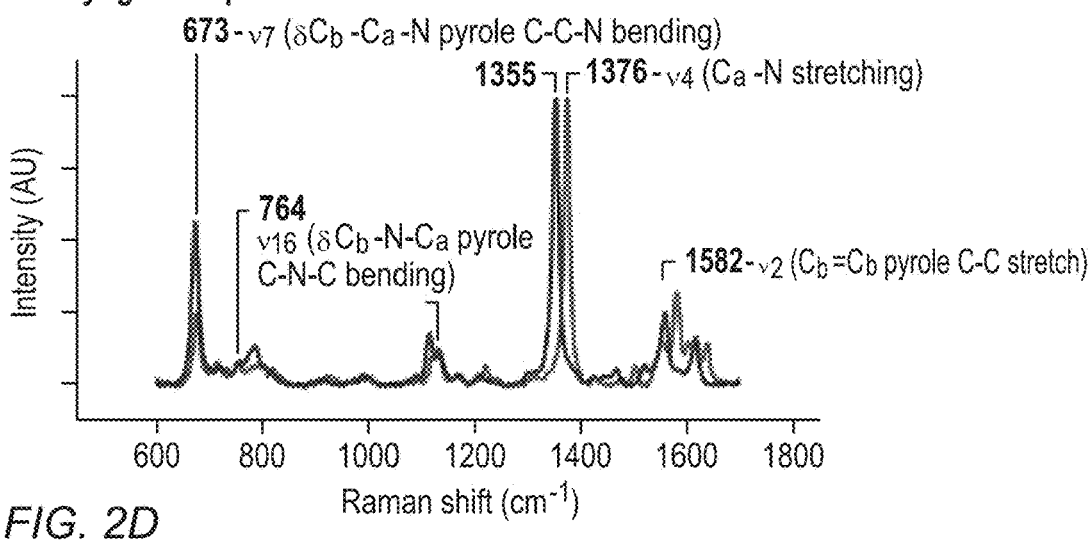
FIG. 2C is a plot of a myoglobin spectrum created using a Raman spectrometer. The peak locations and vibrational mode assignments are known in the scientific literature.
Figure 2D:
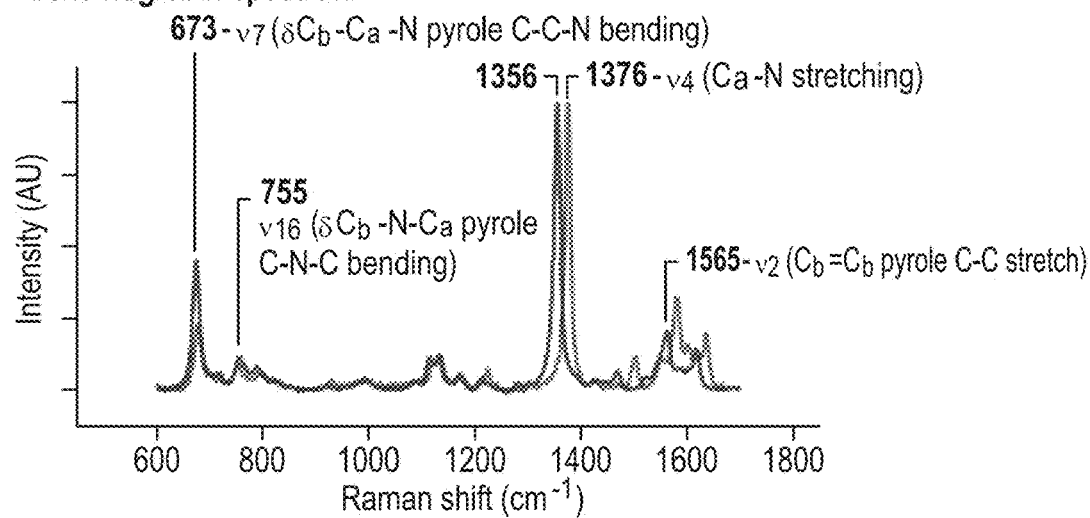
FIG. 2D is a plot of a hemoglobin spectrum created using a Raman spectrometer. The peak locations and vibrational mode assignments are known in the scientific literature.

Hemoglobin, myoglobin, and mitochondrial cytochromes have strong absorption and resonance properties in the near-UV range. FIGS. 2A-2D depicts data from reference samples measured using an RRS device, with the sharp peaks of oxy and deoxy (oxidized and reduced) chromophores. Furthermore, the resonant Raman effect is so specific that hemoglobin, myoglobin mitochondria, or individual cytochromes can be distinguished in a combined sample. FIGS. 2B-2D show resonance Raman spectroscopy of oxygen hemoglobin, myoglobin, and whole mitochondria in oxidized and reduced states, demonstrating an ability to distinguish between these chromophores. We used whole mitochondria to develop the library spectra for this chromophore in a reduced and oxidized state. Because whole mitochondria contain several cytochromes, this approach captures the weighted average redox state of the various cytochromes and accounts for their effect on one another in the mitochondrial membrane.

Resonant Raman Spectroscopy System

Figure 3:
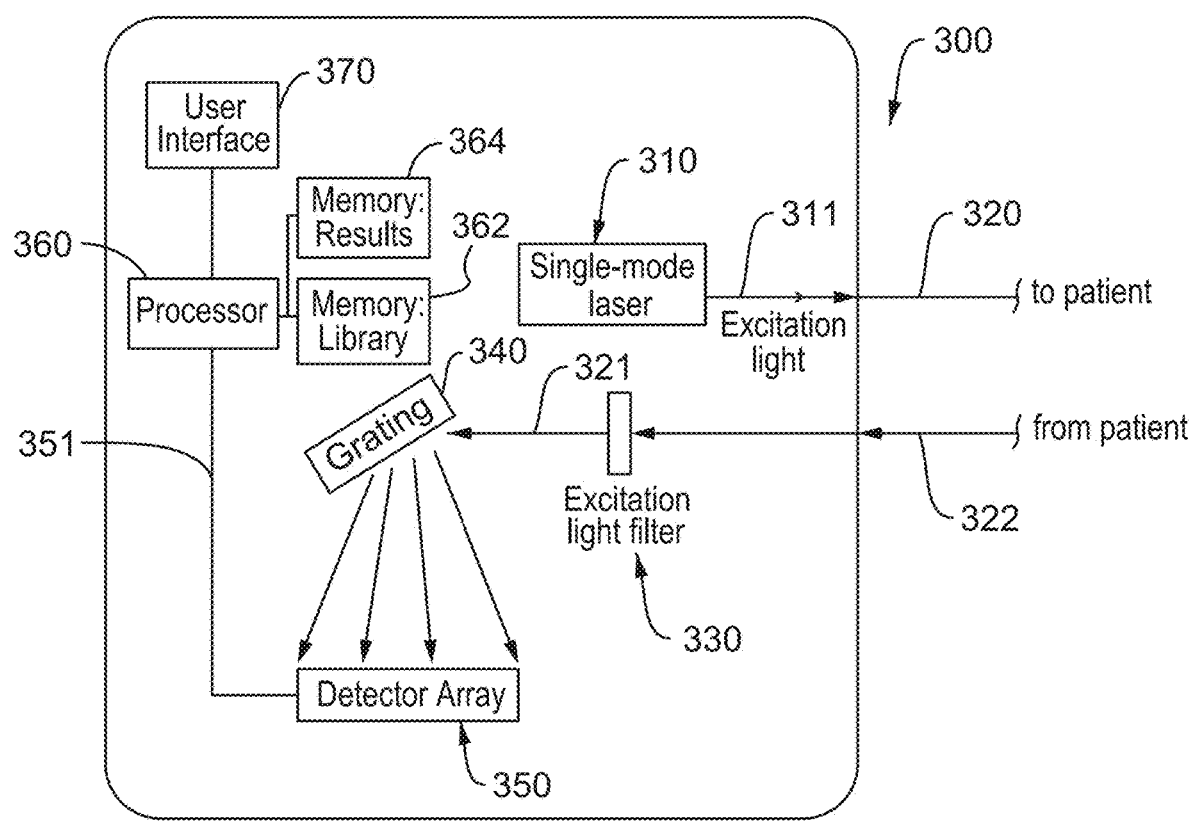
FIG. 3 is a schematic of an inventive resonant Raman spectroscopy (RRS) system.

FIG. 3 shows a (resonant) Raman spectroscopy system 300 for making peri- and post-operative measurements of in vivo, in situ tissue. The system 300 includes a single-mode laser 310 that emits an excitation beam 311 at a wavelength of 390 nm to 460 nm (e.g., about 441 nm). A first optical fiber 320 guides the excitation beam 311 to the subject (not shown), where the excitation beam 311 illuminates a section of the subject's tissue (e.g., a part of the patient's heart, coronary artery, skin, or organs). The subject's tissue responds to the excitation beam 311 by producing Raman-shifted light 321, which is guided by a second optical fiber or fibers 322 to a filter 330 that transmits the Raman-shifted light 321 and attenuates or reflects light at other wavelengths, including the wavelength of the excitation beam 311.

The Raman spectroscopy system 300 includes a spectrometer—here, a grating 340 and detector array 350—that measures the spectrum of the Raman-shifted light 321. In this case, the grating 340 diffracts the different spectral components of the Raman-shifted light 321 at angles proportional to their wavelengths. Each detector element in the detector array 350 monitors the intensity of the signal at a particular angle (wavelength), giving the Raman spectrum. The detector array 350 transmits a signal 351 representing the detected intensity (the Raman spectrum) to a processor 360.

The processor 360 processes the Raman spectrum using a library 362 of Raman spectra for different chromophores stored in a non-volatile computer memory. It generates a weighted sum of the spectra in the library, then compares the weighted sum to the measured Raman spectra. It adjusts the weights to reduce or minimize the difference between the weighted sum and the measured Raman spectra. Once the difference reaches a minimum or falls below a threshold or the elapsed processing time has reached a predetermined limit or stops converging (quickly enough), the processor 360 stops adjusting the weights. It then uses the final weights, which represent the relative concentrations of the chromophores in the tissue, to determine the mitochondrial redox state or the oxygen saturation state of the tissue. (If the laser 310 is tunable, then varying the wavelength of the excitation beam 311 may allow measurement the redox state of individual cytochromes in addition to redox state measurements of the entire mitochondria.) The processor saves these results 364 in the non-volatile computer memory for display to a user via a user interface 370 (e.g., a liquid crystal display).

Figure 8:
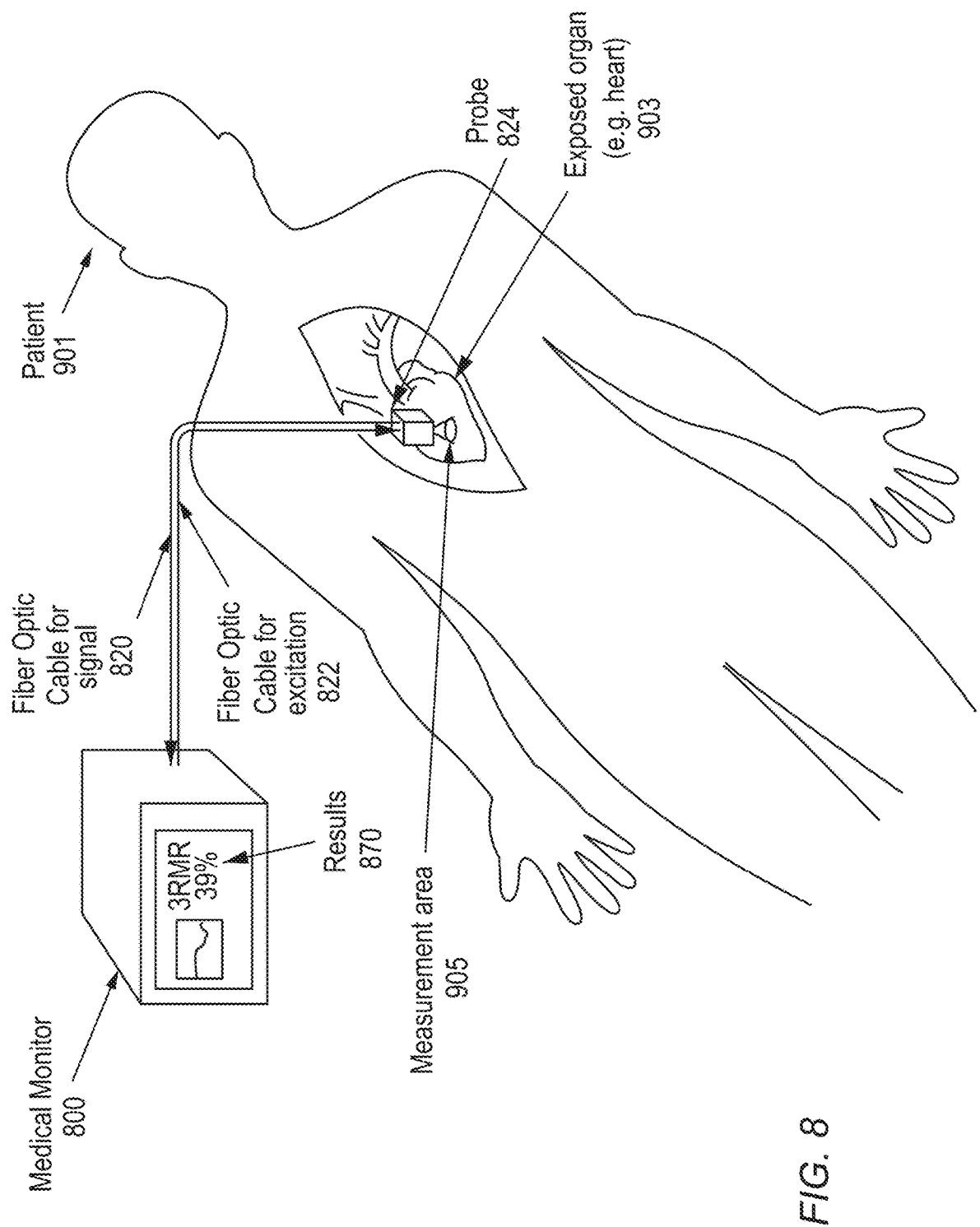
FIG. 8 shows a peri-operative measurement of a person's heart tissue made with the inventive RRS system of FIG. 3.
Figure 9:
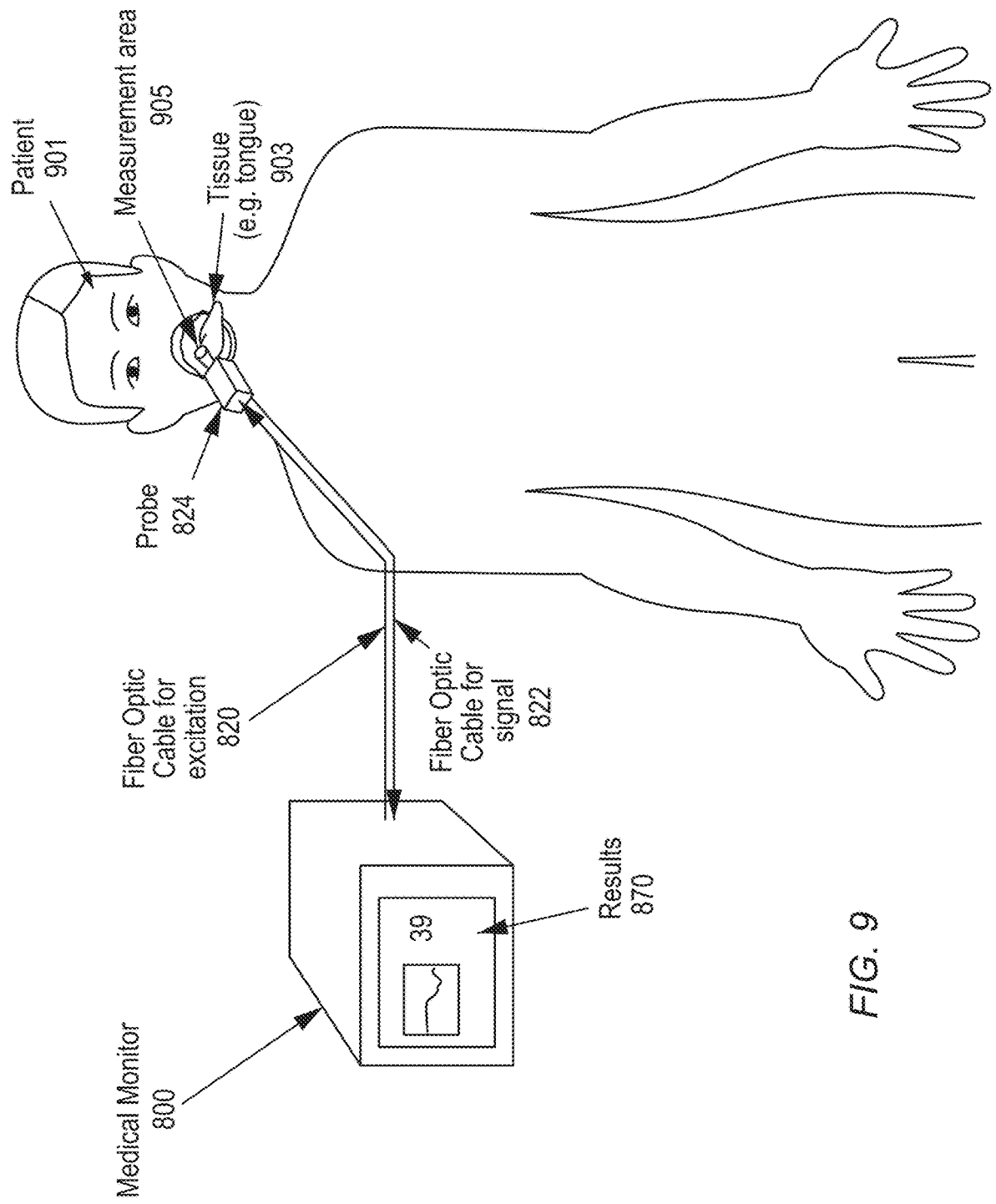
FIG. 9 shows a post-operative/outpatient RRS measurement of a person's tongue made with the inventive RRS system of FIG. 3.

The Raman spectroscopy system 300 of FIG. 3 can be used with a probe (e.g., as shown in FIGS. 8 and 9) to access tissues. The probe may contain optics to focus the laser pump beam 311 onto the collection areas on or in the tissue. The probe also collects and guides the Raman signal 321 via the optical filter 330 to the detector array 350 and the grating 340 with sufficient resolution. The detector array 350 captures the sample spectrum and a reference spectrum from an internal control. The processor 360 coupled to the detector array 350 processes the sample and reference spectra as described below.

Regression Analysis for Determining the Mitochondrial Redox State

Figure 4:
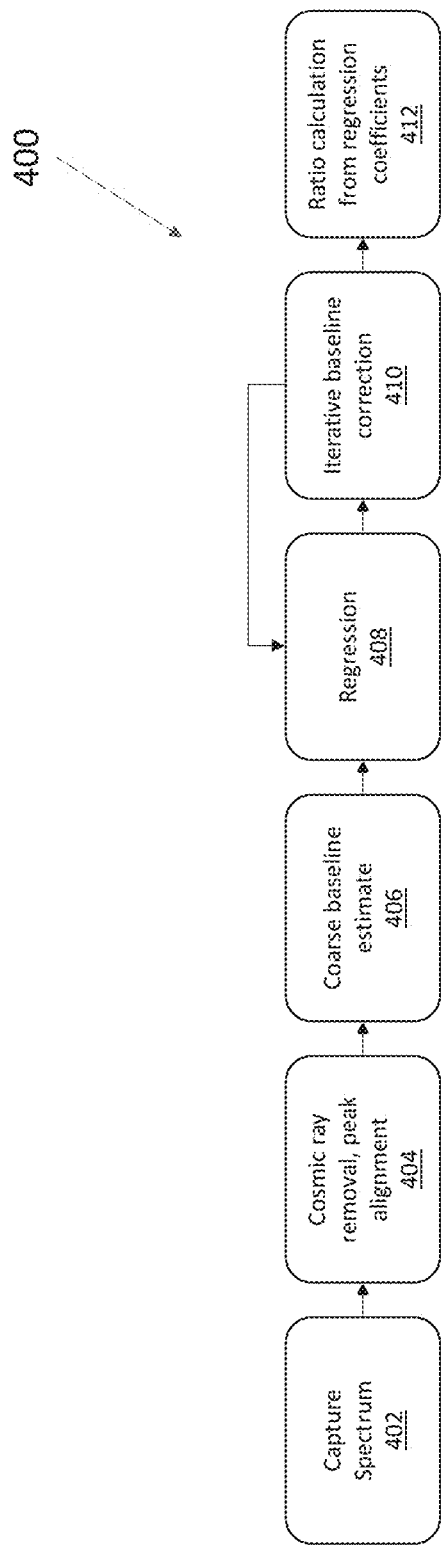
FIG. 4 shows a regression process for determining relative concentrations of chromophores in in vivo, in situ tissue from (resonance) Raman spectra collected using an inventive Raman system.
Figure 5A:
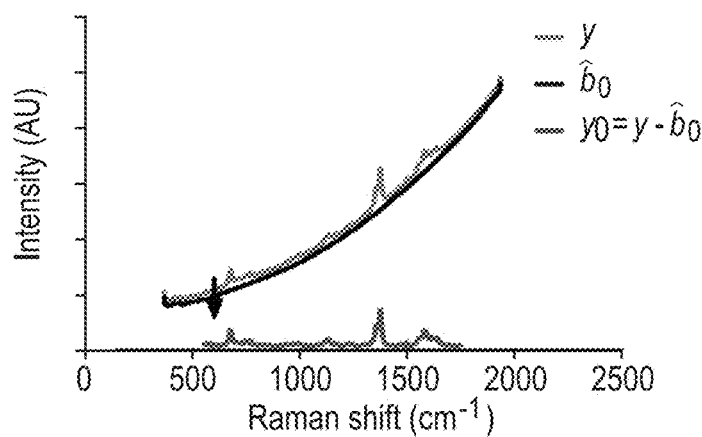
FIGS. 5A-5C illustrate application of the regression process in FIG. 4 to data acquired using an inventive Raman system.
Figure 5B:
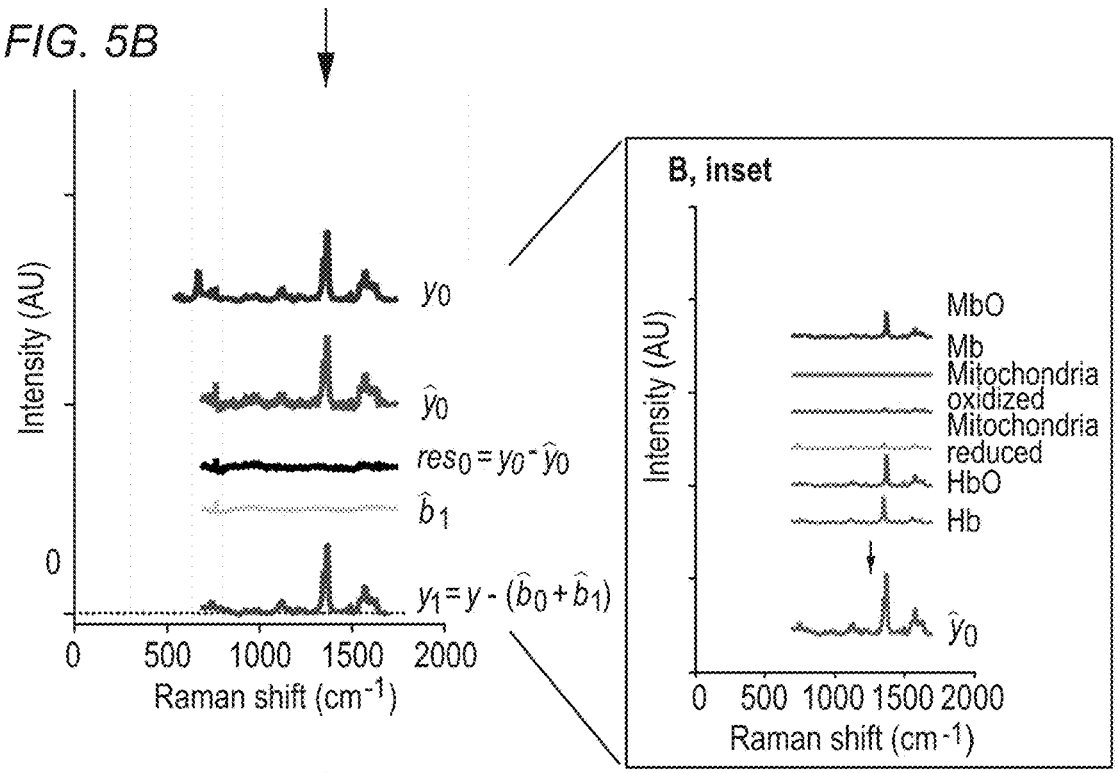
Figure 5C:
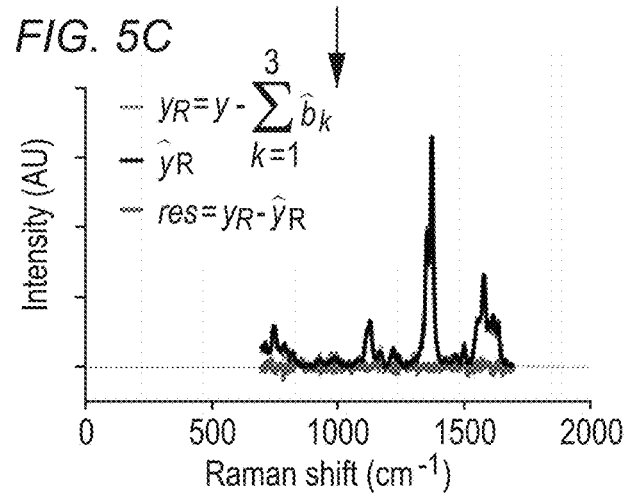

Spectroscopy data can be analyzed by computing Area Under the Curve (AUC) or by comparing specific peak heights. FIG. 4 illustrates a regression process 400 that can be used to determine the relative fractions of chromophores (represented by library spectra) in a spectrum obtained from a combined sample. FIGS. 5A-5C illustrate application of the regression process 400 to experimental data. This regression process 400 can be implemented in real-time or in postprocessing by a processor that is part of or is coupled to an RRS system like the one shown in FIG. 3.

In this regression process 400, the raw spectrum is obtained by averaging the spectrometer readout over a number of seconds (e.g., 180 spectra, each read in 1 second) (402). Very narrow spectral anomalies consistent with cosmic rays are removed from the spectrum (404). In order to correct for any variability in the instrument readout, the spectrum of a known reference sample (for example, acetaminophen) is simultaneously obtained using one of the laser fibers and light at the same excitation wavelength. The reference sample spectrum is compared to the stored spectrum for the reference sample and any shift from known peak positions is added to the raw spectrum (404).

The initial fluorescence baseline is approximated by a slow varying function and subtracted, leaving an estimate of the true Raman spectrum (406; see also FIG. 5A, described below). An iterative baseline refinement (408; see also FIG. 5B) is performed by creating a regression curve as a linear combination of library spectra weighted by regression coefficients. A slow varying curve is fit to any residual spectrum not explained by the regression and is added to the initial baseline. The corrected baseline is then subtracted from the spectrum and the regression performed again (410). This process can be repeated one or many times to improve the baseline estimate. The final result is the relative coefficients of the chromophores from the final regression iteration and the remaining unexplained residual spectrum (412; see also FIG. 5C).

This regression process 400 has several advantages, including the advantage of accounting for small spectral features across the entire spectral range in order to precisely determine relative concentrations. Relative concentrations can then be used to accurately determine oxygen saturation percentage or a ratio of reduced chromophores to total (i.e., oxidized and reduced) chromophores. The oxygen saturation of hemoglobin, for example, can be calculated as a ratio of the regression coefficient (k) of the oxy component to the sum of the regression coefficients of the oxy and deoxy components as follows:

$$S_{HbO_2} = \frac{k_{oxyHb}}{k_{oxyHb} + k_{deoxyHb}}$$

FIGS. 5A-5C illustrate regression using experimentally acquired Raman data. FIG. 5A shows a coarse baseline estimation: the processed, averaged, spectrum y gathered by the device, includes a potent fluorescent baseline. A coarse estimate of this baseline, $\hat{b}_0$ is obtained by jointly estimating fifth order polynomial coefficients and library spectra coefficients using a linear regression. The first iteration of the true resonance Raman spectrum is thus given by $y_0 = y - \hat{b}_0$.

FIG. 5B shows iterative baseline refinement: A composite regression curve $\hat{y}_0$, which most closely fits $y_0$ is then calculated from a linear combination of library spectra weighted by regression coefficients. A slow-varying cubic spline fit to the residual $res_0 = y_0 - \hat{y}_0$, denoted by $\hat{b}_1$ is added to the initial baseline to include any slow wobbles in the baseline that were not captured by the polynomial fit. The inset of FIG. 5B shows components of $\hat{y}_0$ include oxyhemoglobin (HbO), deoxyhemoglobin (Hb), oxymyoglobin (MbO), deoxymyoglobin (Mb), and oxidized and reduced mitochondrial spectra. In FIG. 5C, the iterative baseline fitting procedure is repeated thrice to obtain the final estimate ($\hat{y}_R$). The residual (res) is calculated by subtracting the final regression curve ($\hat{y}_R$) from the baseline adjusted spectrum ($y_R$).

Chromophore Enhancement

Because each chromophore is optimally enhanced near its individual absorption peak, selecting an excitation wavelength closer or further from the absorption peak changes the peak height of the measured Raman spectrum. By including experimentally determined enhancement factors in the saturation or redox calculation, the accuracy of the result is dramatically improved. To determine the enhancement factors, a known volume of chromophore is suspended in a liquid at a known concentration and a Raman spectrum is collected. The spectrum is scaled such that the height of a characteristic spectral peak (the v4 band) is one. The number used to scale the spectrum is the enhancement factor. Multiplying a spectrum in a measured sample by the enhancement factor adjusts it for the relative strength of the enhancement at that excitation wavelength. Excitation wavelengths may be chosen for optimal enhancement or to influence the penetration depth of the light in tissues.

Figure 6:
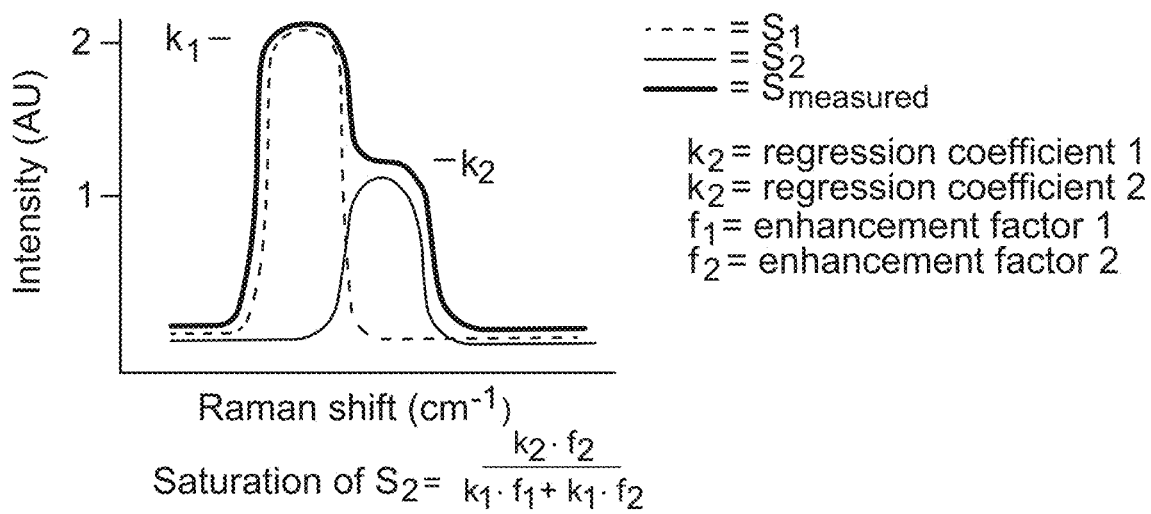
FIG. 6 shows a method for normalizing spectra by use of an enhancement factor to account for differential resonance of each molecule at various excitation wavelengths.

FIG. 6 illustrates how enhancement factors can be used to account for amplitude variations in the spectral resonance(s) of each molecule with excitation wavelength. Put differently, these enhancement factors represent how the peaks in the spectrum for each molecule (chromophore) increase or decrease due to a change in the excitation wavelength. In this case, the measured Raman spectrum $S_{measured}$ is decomposed as the sum of the spectra $S_1$ and $S_2$ for two chromophores weighted by regression coefficients $k_1$ and $k_2$, respectively. The spectra $S_1$ and $S_2$ are from a library of predetermined or previously measured spectra.

When corrected for the enhancement factors, the saturation of the spectrum $S_2$ for the second chromophore is given by:

$$\text{Saturation of } S_2 = \frac{k_2 f_2}{k_1 f_1 + k_2 f_2}$$

where $f_1$ and $f_2$ are the enhancement factors for the first and second chromophores, respectively. If the height of library peak $S_1$ is twice the height of library peak $S_2$, then the enhancement factor $f_1$ is 0.5 and the enhancement factor $f_2$ is 1.0. Thus, in the case of 50% saturation, $S_1$ is twice the height of $S_2$ (i.e., $k_1 = 2$ and $k_2 = 1$).

Absolute Concentration, Relative Concentration, and Myoglobin Index

The spectroscopy results according to the present technology may be for absolute concentration (such as absolute concentration of hemoglobin in the tissue) or for relative concentration. Examples of relative concentrations include ratios of oxidized mitochondria to reduced mitochondria, or oxyhemoglobin with deoxyhemoglobin, or oxymyoglobin to deoxymyoglobin. The signal from myoglobin may be used as an index to convert a signal strength of another chromophore into a relative concentration for a volume of tissue. The signal strength for myoglobin represents a fixed mass of tissue that makes up the interrogation volume of the excitation light (see FIG. 7, described below). Because myoglobin concentrations are similar for tissues of the same type, dividing a chromophore measurement by the total (oxy- and deoxy-) myoglobin signal generates a relative concentration. For example, the mitochondria to myoglobin ratio can be compared to a known normal. Similarly, the hemoglobin to myoglobin ratio can be used to represent the concentration of blood in the tissue. Using other wavelengths of light, the amount of water could be compared to myoglobin in order to evaluate edema.

Figure 7:
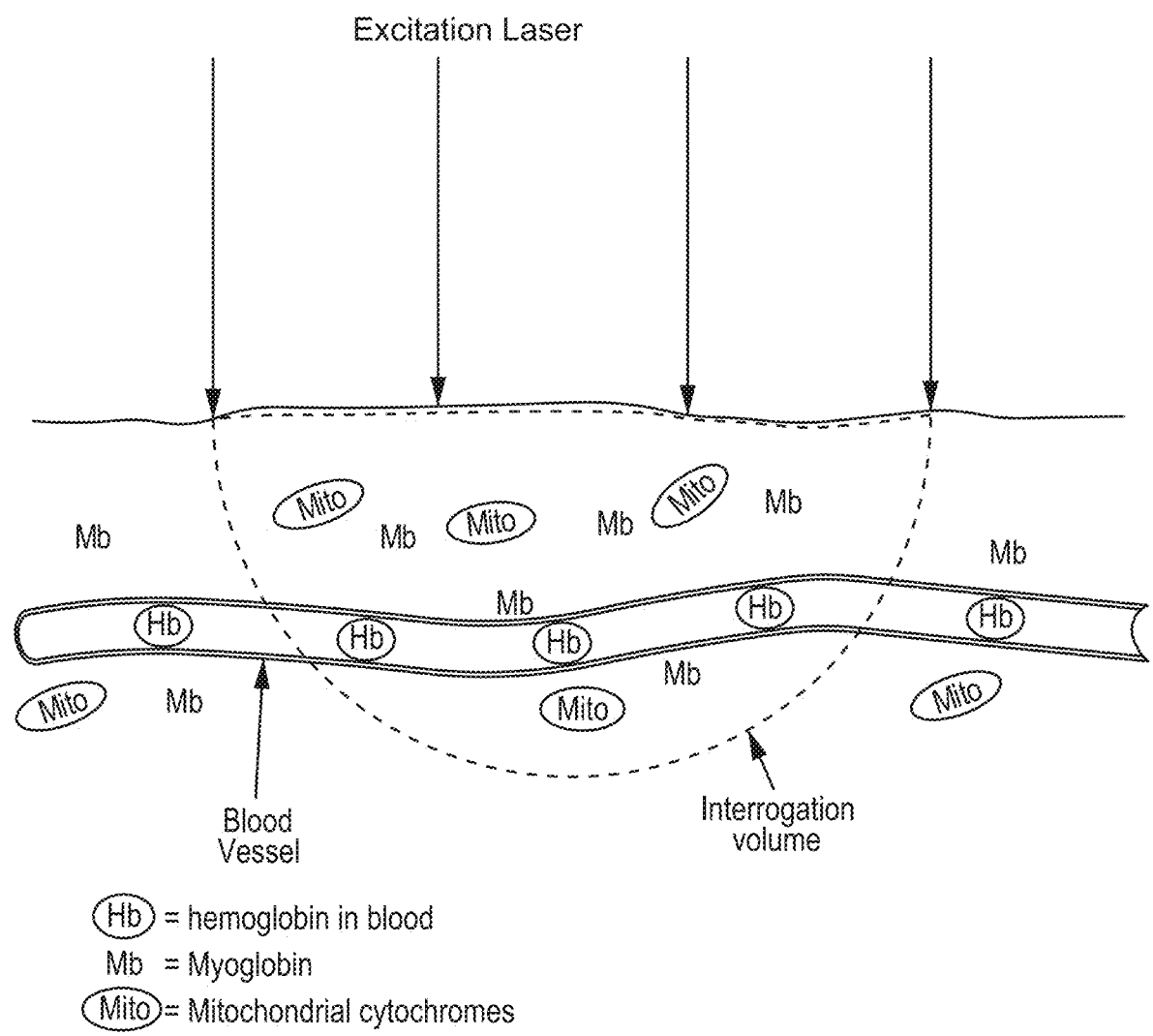
FIG. 7 illustrates a (resonance) Raman spectroscopy measurement of the myoglobin index of (living) tissue.

FIG. 7 shows that incoming light is absorbed in a volume of tissue by the hemoglobin, myoglobin, and mitochondria in the tissue, as these are the principal absorbers of the light. Since the concentration of these molecules is inhomogeneous across the tissue, the absorption volume is unknown, making it difficult to calculate an absolute concentration (versus saturation, which is a ratio). By dividing by the total myoglobin signal, it is possible to create an index (e.g., a myoglobin index equal to the mitochondria signal/myoglobin signal) that is normalized for tissue volume.

The spectroscopy results according to the present technology advantageously are available on the order of seconds. Signal processing and computer processes may be used to process the spectroscopy data.

Another preferred embodiment of the present technology provides a medical measurement device comprising: a laser source (such as a laser tunable to multiple wavelengths), a spectrometer with multiple wavelength settings for resonance Raman spectroscopy; and a biological probe optically connected to the spectrometer (e.g., as shown in FIG. 3).

The device can obtain resonance Raman spectra at a variety of wavelengths corresponding to the "fingerprint" or "signature" of molecules associated with tissue oxygen metabolism (such as hemoglobin (Hb), myoglobin (Mb), and the mitochondrial cytochromes in complexes I, III, and IV. One or multiple excitation wavelengths may be used in order to optimize spectra from each target molecule. In the case of multiple wavelengths, redox states may be determined for the combined mitochondria or for individual cytochromes which may be analyzed individually or as a vector indicating the risk of impending failure. Signal processing may include multiple moment of the data including the absolute value, the rate of change, or the integrated time above a certain value.

Devices may be used in the operating room to examine target molecules and the status of various organs such as the liver, GI tract, brain or heart or other tissues of interest (e.g., as in FIG. 8, described below). Implantable probes may be placed in transplanted tissues to allow for their interrogation at subsequent time points to monitor for rejection.

Raman Spectroscopy Methods for In Vivo Peri-Operative Monitoring

The Raman spectroscopy systems shown in FIGS. 1 and 3 can be used to monitor patents in inpatient and outpatient settings. In operation, an inventive system monitors a patient by interrogating tissue chromophores in vivo and in-situ in a biological tissue using Raman spectroscopy. The system quantifies the mitochondrial redox state using regression on the acquired Raman spectrum. For instance, the system can determine the relative concentrations of multiple chromophores based on one or more combinations of an entire reference spectrum for each chromophore.

In some cases, the system measures the redox state of whole mitochondria in order to capture the in-situ state of multiple cytochromes and their effect on one another. The redox state measured by the system can be a combination of one or more of hemoglobin oxygen saturation, myoglobin oxygen saturation, and/or the redox state of individual cytochrome complexes in the mitochondria.

Examples of the biological organs that can be characterized with the present technology include the brain, heart, liver, tongue or other oral mucosa, the esophagus, peripheral skeletal muscle, intestines, pancreas, kidney, bladder, urethra, cervix, uterus, oropharynx, nasopharynx, etc.

The inventive methods include monitoring a specific tissue bed (brain, heart, lung, liver, etc.) in the patient, e.g., by placing a probe on or near any mucosal or epithelial covered surface of a body or an organ.

Examples of spectroscopy results acquired with the present technology include, e.g., data relating to diagnosing and/or following progression or resolution of organ failure and/or tissue injury, and/or tissue ischemia; determining whether the tissue has insufficient oxygen delivery to meet metabolic demands of the tissue while simultaneously determining whether mitochondrial dysfunction or injury exists; determining tissue viability; and/or diagnosing tissue injury. Example spectroscopy results may relate to diagnosing impending organ failure.

Example spectroscopy results according to the present technology may yield data for tissue hemoglobin oxygen saturation including amount of oxyhemoglobin and deoxyhemoglobin by Raman spectroscopy; data for oxygenated hemoglobin, deoxygenated hemoglobin; data for myoglobin oxygenation saturation; data for mitochondrial cytochrome redox status.

The system may determine or be programmed with a threshold value for a redox marker and use that threshold value to predict organ failure. For example, the system may interrogate in vivo, in-situ biological tissue with Raman spectroscopy to quantify the redox marker. It may use this redox marker to determine the adequacy of tissue protection during surgery and to predict tissue function following reperfusion of the tissue.

The system may analyze Raman spectroscopy results by referencing them to the strength of the myoglobin signal in order to establish an index that is referenced to a volume of tissue (e.g., as illustrated in FIG. 7). The system may analyze Raman spectroscopy results to identify changes in cytochrome conformation that indicate permanent cellular damage or apoptosis. For instance, the system may detect cytochrome c release from the inner mitochondrial membrane.

Depending on the setting (e.g., inpatient or outpatient), an inventive system may monitor the heart and predict cardiac dysfunction or arrest based on the acquired Raman spectrum. An inventive system can also monitor an organ in the body and predict organ dysfunction or rejection based on the acquired Raman spectrum. It can also monitor the adequacy of coronary transfer for bypass operations; monitor organ health before, during, and/or after an organ transplant surgery; and/or monitor the health of a skin graft or skin flap.

FIGS. 8 and 9 show how the Raman spectroscopy system 300 can be used to monitor a patient 901. In FIG. 8, the Raman spectroscopy system 300 is used to make a peri-operative measurement of a patient's organ tissue 903. An incision in the patient's skin exposes the organ tissue 903 (e.g., heart tissue).

A probe 824 is coupled to the distal ends of the first and second optical fibers 320 and 322. Optics in the probe 824 focus the excitation beam 311 to a point on or within the organ tissue 903 and couple Raman-shifted light 321 from the tissue 903 into the second optical fiber or fibers 322. For example, the probe 824 may include a spectral filter that filters the excitation beam 311 to ensure a narrow laser linewidth. The probe 824 focuses the light onto a small area (typically 1-4 mm in diameter) on the surface of the tissue. The probe's collection optics are configured such that the majority of scattered light is coupled into the collection fiber 322. The collection optics may also contain a filter (e.g., in addition to or instead of the filter 330) to reject light at the excitation wavelength and to accept Raman-shifted light from the region of interest. The probe may be further configured to attach directly to the patient's tissue or to be contained within a sterile cover or sleeve to prevent contamination of tissues.

A surgeon can use the system 300 to make RRS measurements before, during, and after surgery and view the mitochondrial redox state in real-time on the system's user interface 370. For instance, the surgeon may use the mitochondrial redox state to determine if a damaged tissue is viable (e.g., after a burn). During surgery, the surgeon may monitor an ischemic tissue (e.g., an ischemic heart during cardiac bypass or an isolated heart awaiting transplant) to assess the adequacy of storage conditions. Before, during, and after reperfusion of an ischemic tissue, the surgeon may use the mitochondrial redox state to predict the function of the re-perfused tissue. If the mitochondrial redox state predicts tissue failure, the surgeon may change the surgical strategy (e.g., a change or continue cardiac bypass interventions) or intervene with other medical treatments.

FIG. 9 shows the Raman spectroscopy system 300 being used for a post-operative measurement of a patient 901. In this case, the probe 824 illuminates and collects Raman-shifted light from a measurement area 905 on more readily accessible tissue—the tongue 903. The system 300 displays the mitochondrial redox state of the illuminated tongue tissue on the user interface 370. The mitochondrial redox state, myoglobin oxygen saturation, or hemoglobin oxygen saturation changes in response to systemic changes in oxygen delivery, such as changes in blood volume, blood hemoglobin concentration, cardiac output, or infection (e.g., during septic shock). Either as a direct effect (less oxygen delivered) or a secondary effect (local vascular responses to systemic circulation), local tissue oxygen saturation or mitochondrial redox states may change. The healthcare provider may use this information as an early warning of systemic changes in oxygen delivery in order to initiate or change medical therapies (e.g., to increase blood volume with fluids or transfusion or to increase inotropic drugs to increase cardiac output).

Experimental Results of In Vivo Experimentation

Techniques according to the present technology have been successfully applied to the myocardium in animals, demonstrating feasibility. Techniques according to the present technology require no probe contact (although probe contact with tissue can take place if desired) with tissue and acquisition times are on the order of seconds.

A peri-operative measurement device was constructed with a 441 nm laser excitation source, a fiber optic cable, and an optical probe that focuses on a spot of myocardial tissue (FIG. 9). Light is returned to the device through a bundle of fiber optic cables. The laser wavelength is filtered out and the light is focused on a grating which separates it by wavelength onto a CCD. The CCD is periodically read and the 2D image converted into a Raman spectrum for further analysis which is completed by custom software running on an attached computer.

Figure 10A:
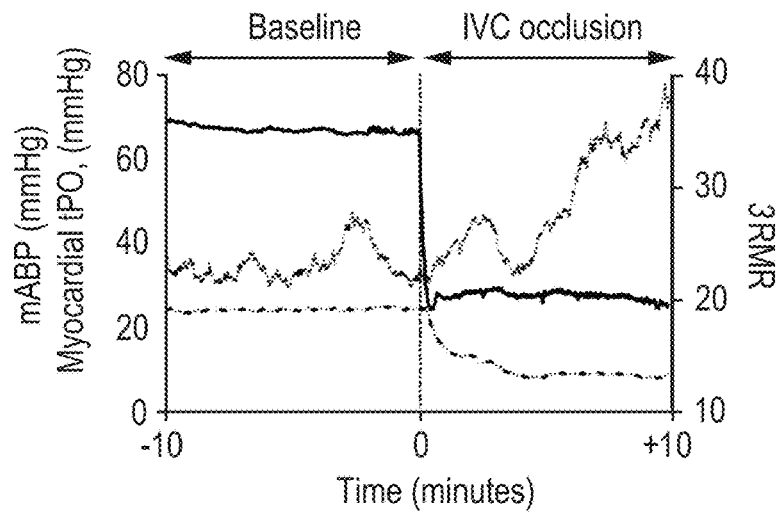
FIGS. 10A-10C show measurements of ischemia in rat myocardium made using an inventive resonance Raman spectroscopy (RRS) system.
Figure 10B:
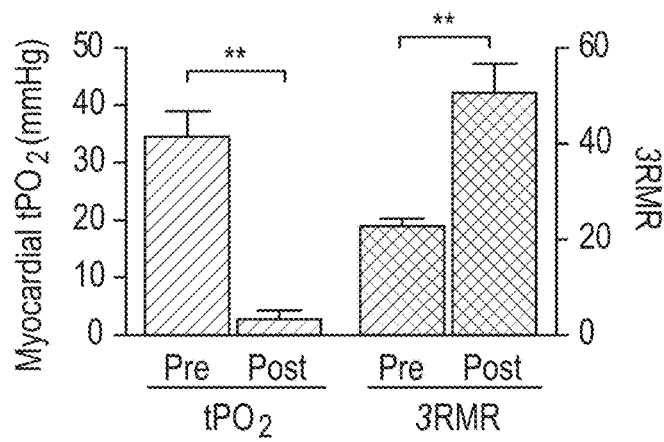
Figure 10C:
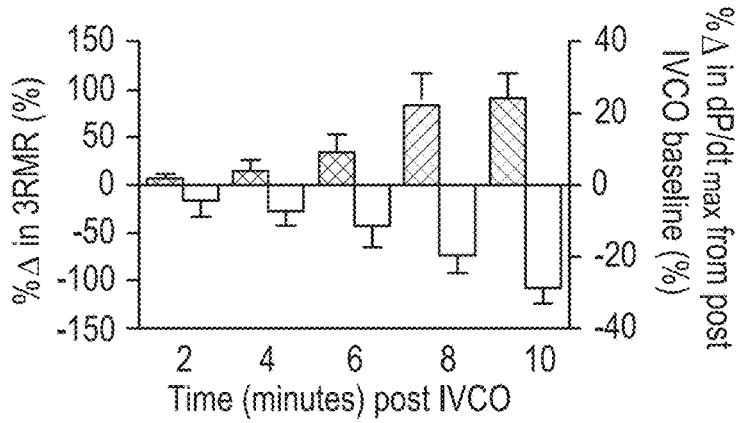

FIGS. 10A-10C show resonance Raman spectroscopy data collected using this peri-operative measurement device from rat myocardium during in vivo occlusion of the inferior vena cava. FIG. 10A shows tissue oxygen tension (tPO2, dot-dashed line) following complete inferior vena cava occlusion (IVCO). The tPO2 decreased from a baseline of 25 mmHg to 10 mmHg within 2 minutes. The increase in resonance Raman reduced mitochondrial ratio (3RMR, the ratio of reduced mitochondrial Raman signal to the total mitochondrial Raman signal) signal (dotted line) was delayed from this decrease in tPO2 by 2-3 minutes (integration time is 3 minutes). Mean arterial blood pressure (mABP, solid line) decreased abruptly following IVCO as is typical for acute changes in myocardial preload. N=1 representative sample. FIG. 10B shows myocardial tPO2 after 10 minutes of IVCO (post). The myocardial tPO2 decreased significantly (P=0.0020) and 3RMR increased significantly (P=0.0040, paired t test). *, P<0.05. FIG. 10C shows that acute IVCO caused an abrupt decrease in myocardial preload, which decreased contractility (defined here as dP/dTmax) significantly. From this new (i.e., post-occlusion) baseline, 3RMR (black bars) increased and was associated with a trend towards decreasing contractility (white bars) (P=0.06, linear regression). In FIGS. 10B and 10C, data are means and error is SEM. n=10 animals.

Figure 11A:
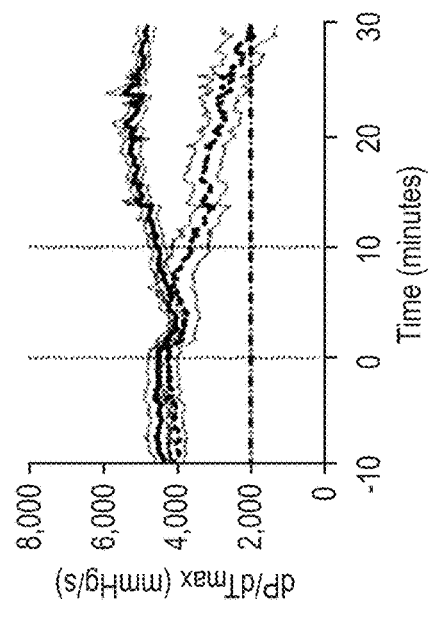
FIGS. 11A-11F show measurements of hypoxia in rat myocardium made using an inventive RRS system.
Figure 11B:
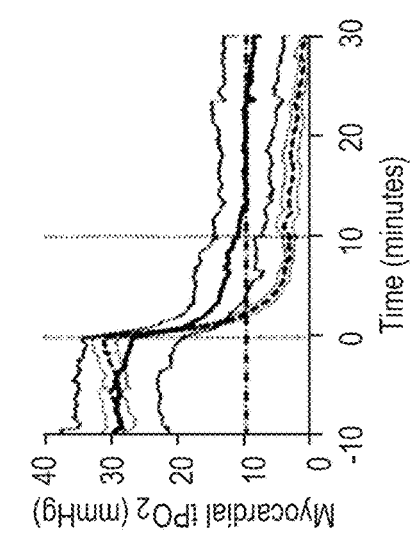
Figure 11C:
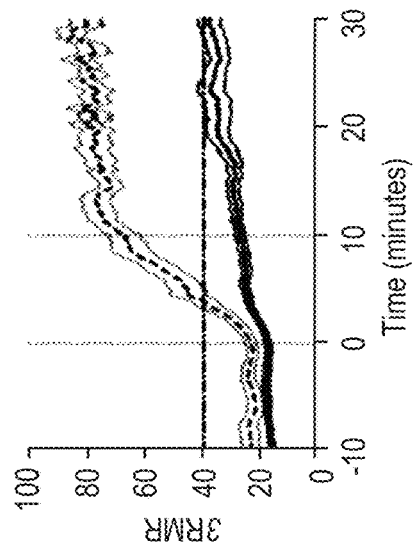

FIGS. 11A-11F show Raman-based oxygenation and hemodynamic data collected using the peri-operative measurement device from two groups of animals, separated by 3RMR at 10 minutes. FIG. 11A shows 3RMR values over time in animals in which 3RMR at 10 minutes exceeded 40% (dashed line, n=12) and those in which it was at or below 40% at 10 minutes of hypoxia (solid line, n=19) were significantly different (P<0.0001, repeated measures ANOVA with Bonferroni correction). FIG. 11B shows that in animals with higher 3RMR, myocardial tPO2 was significantly lower than in animals with a low 3RMR at 10 minutes (P=0.001, repeated measures ANOVA with Bonferroni correction). FIG. 11C shows that myocardial contractility (dP/dTmax) was similar between groups at 10 minutes (P=0.065) but was significantly lower in the high 3RMR group by 30 minutes (P<0.0001), suggesting the inability to increase contractility in response to hypoxemia. Data are means and error (shaded) is SEM in FIGS. 11A-11C.

Figure 11D:
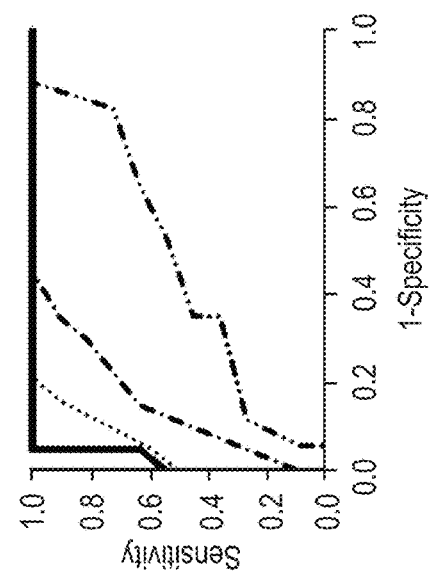
Figure 11E:
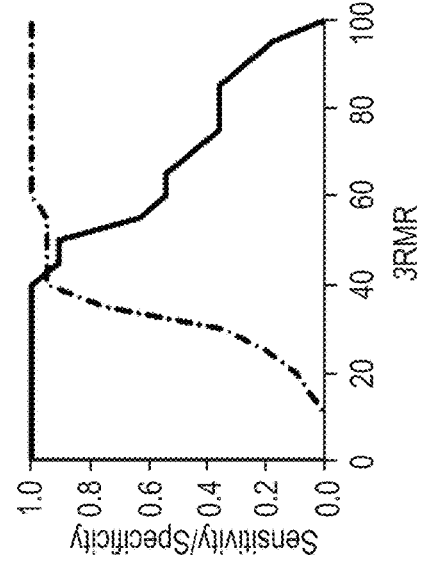
Figure 11F:
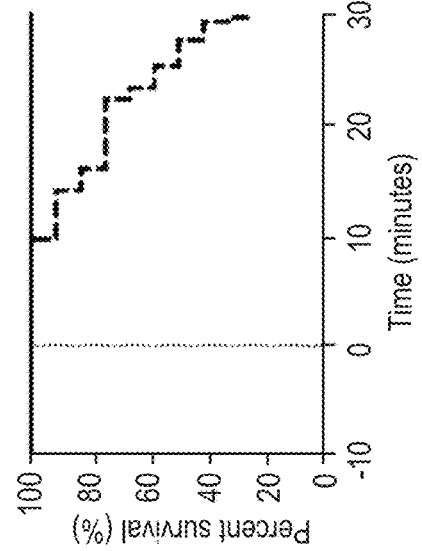

FIG. 11D shows that animals in the higher 3RMR group exhibited a significantly higher incidence of cardiac arrest within the 30-minute observation period compared with those in the lower 3RMR group (P<0.0001, log rank test). FIG. 11E shows sensitivity (solid black) and specificity (dotted black) for 3RMR values at 10 minutes as predictive of cardiac arrest within 30 minutes were jointly maximized at a threshold 3RMR value of 40%. FIG. 11F shows receiver operating characteristics plot of 3RMR (solid red, AUC 0.98), tissue oxygen tension (dotted black, AUC 0.93), tissue oxyhemoglobin saturation (dot-dash, AUC 0.82), and ejection fraction (orange dot-dash, AUC 0.39) measurements at 10 minutes as diagnostic tests predicting impending cardiac arrest in the following 20 minutes.

Figure 12A:
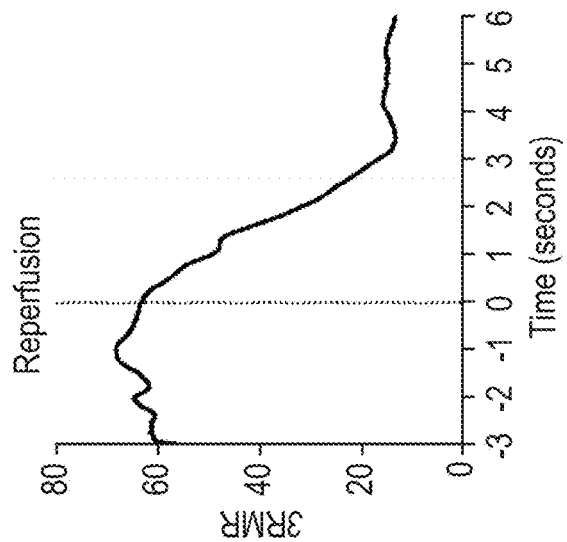
FIGS. 12A-12D show measurements of ischemia and reperfusion in swine made using an inventive RRS system.
Figure 12B:
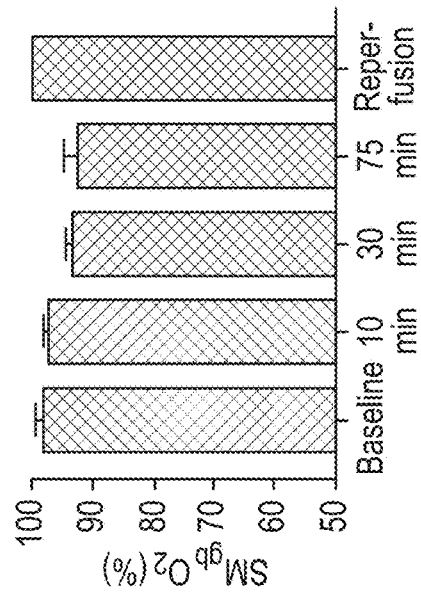
Figure 12C:
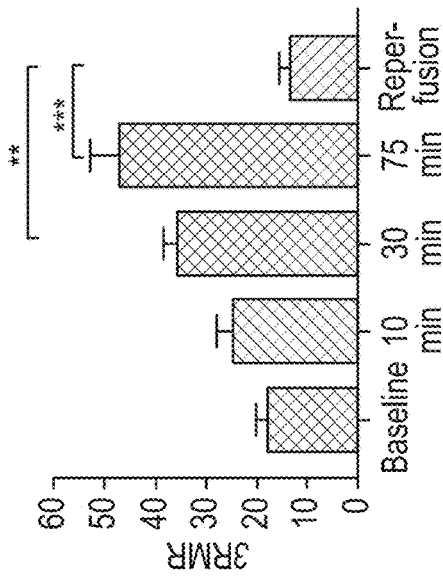
Figure 12D:
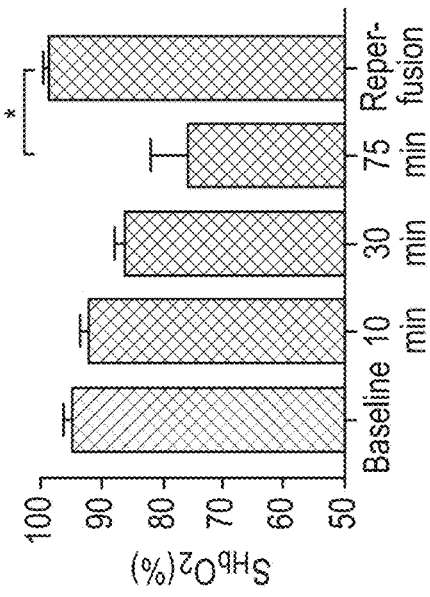

FIGS. 12A-12D shows resonance Raman spectroscopy data collected using the peri-operative measurement device from the myocardium of swine undergoing aortic cross-clamping and subsequent reperfusion. FIG. 12A shows that in swine, 3RMR was 18.2±6.3% at baseline, increased to 47.1±16.2% following 75 minutes of ischemic time, and then decreased to 13.8±5.3% 3 minutes following reperfusion (P=0.0002, repeated measures ANOVA with Bonferroni correction). FIG. 12B shows that following myocardial reperfusion with cardiopulmonary bypass, 3RMR decreased to near baseline levels within 3 minutes (n=1, representative sample). FIG. 6C shows that RRS-based tissue oxyhemoglobin saturation ($S_{Hb}O_2$) decreased during ischemia, also returning to baseline levels during reperfusion (P=0.01). And FIG. 12D shows that oxymyoglobin saturation ($S_{Mb}O_2$) did not change significantly during ischemia (P=0.34). (A, C) *, P<0.05; , P<0.01; *, P<0.001. In FIGS. 12A-12D, all data are means, error is SEM.

From the experimental data set forth above, it may be seen that with the use of resonance Raman spectroscopy, monitoring of several tissue chromophores can be performed, for predicting organ dysfunction or failure in vivo. Various states of hypoxia and ischemia are amenable to quantification using resonance Raman spectroscopy.

Outpatient applications also are provided. Depending on the sensitivity of the device, the technology of the present technology may be used in the outpatient setting for determination of various target compounds such as the mitochondria or hemoglobin, for example, on the tongue in order to understand whole body perfusion and oxygen supply. The device may be used to diagnose certain precancerous or cancerous lesions (such as skin melanoma, etc.) in vivo based on their oxygen usage compared to surrounding tissues. Point of care or continuous real-time tissue monitoring is provided with the inventive method and its components (e.g., as shown in FIG. 9).

The inventive methods and devices may be used to evaluate the oxygen status of any organ during surgery (e.g., the heart during cardiopulmonary bypass surgery, the brain during neurosurgery, and various organs during transplant); to evaluate donor organs prior to transplant; to include in devices such as pacemakers to interrogate areas of myocardium at risk of injury; to evaluate a patient with congestive heart failure (such as at the hospital, office, home, etc.); and/or to determine symptom etiology (such as fluid overload versus deterioration in heart function). The inventive methods and devices may also be used for evaluation of any general shock state (trauma, cardiogenic, septic). Applications include hypoxic-hypoxia, hemorrhagic shock, cardiogenic shock, septic shock, and isolated organ ischemia (including wounds).

While the present technology has been described in terms of its preferred embodiments, those skilled in the art will recognize that the technology can be practiced with modification within the spirit and scope of the appended claims.

The invention claimed is:

1. A method of monitoring a patient, the method comprising:
  measuring a resonance Raman spectrum of in vivo, in situ tissue of the patient with a Raman spectroscopy system; and
  quantifying a mitochondrial redox state of the in vivo, in situ tissue based on the resonance Raman spectrum,
  wherein quantifying the mitochondrial redox state comprises:
    performing a regression analysis of the resonance Raman spectrum using a linear combination of reference resonance Raman spectra from whole mitochondria in reduced and oxidized states, the reference resonance Raman spectra representing weighted average redox states of cytochromes in the whole mitochondria and effects of the cytochromes on each other in a mitochondrial membrane of the whole mitochondria; and
    determining a redox state of whole mitochondria in the in vivo, in situ tissue based on the regression analysis of the resonance Raman spectrum.

2. The method of claim 1, wherein quantifying the mitochondrial redox state additionally comprises determining at least one of a hemoglobin oxygen saturation, a myoglobin oxygen saturation, or a redox state of individual cytochrome complexes in mitochondria of the in vivo, in situ tissue.

3. The method of claim 1, further comprising:
  determining an organ dysfunction of the patient based on the mitochondrial redox state of the in vivo, in situ tissue.

4. The method of claim 3, wherein the in vivo, in situ tissue comprises heart tissue and the organ dysfunction comprises at least one of cardiac dysfunction or cardiac arrest.

5. The method of claim 1, further comprising:
  predicting at least one of organ dysfunction of the patient or organ rejection by the patient based on the mitochondrial redox state of the in vivo, in situ tissue.

6. The method of claim 1, wherein measuring the resonance Raman spectrum occurs during surgery on the in vivo, in situ tissue, and further comprising:
  determining adequacy of tissue protection during surgery based on the mitochondrial redox state of the in vivo, in situ tissue; and
  predicting tissue function following reperfusion of the in vivo, in situ tissue based on the mitochondrial redox state of the in vivo, in situ tissue.

7. The method of claim 1, wherein the in vivo, in situ tissue comprises myocardial tissue and measuring the resonance Raman spectrum occurs during and after cardiac bypass.

8. The method of claim 1, wherein the in vivo, in situ tissue comprises coronary tissue and measuring the resonance Raman spectrum occurs during bypass surgery.

9. The method of claim 1, wherein the in vivo, in situ tissue comprises organ tissue and measuring the resonance Raman spectrum occurs during organ transplant surgery.

10. The method of claim 1, wherein the in vivo, in situ tissue comprises at least one of a skin graft or a skin flap.

11. The method of claim 1, wherein performing the regression analysis comprises scaling the resonance Raman spectrum by an enhancement factor selected to account for amplitude variations in spectral resonance of molecules in the whole mitochondria with an excitation wavelength used to generate the resonance Raman spectrum.

12. The method of claim 1, wherein generating the resonance Raman spectrum comprises illuminating the in vivo, in situ tissue at each of a plurality of excitation wavelengths.

13. A system for monitoring a patient, the system comprising:
  a laser to generate an excitation beam;
  a probe, in optical communication with the laser, to illuminate in vivo, in situ tissue of the patient with the excitation beam and to collect a Raman signal emitted by the in vivo, in situ tissue in response to the excitation beam;
  a spectrometer, in optical communication with the probe, to generate a resonance Raman spectrum from the Raman signal; and
  a processor, operably coupled to the spectrometer, to quantify a mitochondrial redox state of the in vivo, in situ tissue based on the resonance Raman spectrum,
  wherein the processor is configured to quantify the mitochondrial redox state by:

(i) performing a regression analysis of the resonance Raman spectrum using a linear combination of reference resonance Raman spectra from whole mitochondria in reduced and oxidized states, the reference resonance Raman spectra representing weighted average redox states of cytochromes in the whole mitochondria and effects of the cytochromes on each other in a mitochondrial membrane of the whole mitochondria; and (ii) determining a redox state of whole mitochondria in the in vivo, in situ tissue based on the regression analysis of the resonance Raman spectrum.

14. The system of claim 13, wherein the laser is a single-mode laser configured to emit the excitation beam at a wavelength of 441 nm and a power of about 4 mW.

15. The system of claim 13, wherein the spectrometer has a Full Width at Half Maximum (FWHM) resolution of 8 $cm^{-1}$ and an absolute Stokes shift accuracy of <0.4 $cm^{-1}$.

16. The system of claim 13, wherein the processor is configured to quantify the mitochondrial redox state by determining at least one of a hemoglobin oxygen saturation, a myoglobin oxygen saturation, or a redox state of individual cytochrome complexes in mitochondria of the in vivo, in situ tissue.

17. The system of claim 13, wherein the processor is further configured to determine an organ dysfunction of the patient based on the mitochondrial redox state of the in vivo, in situ tissue.

18. The system of claim 17, wherein the in vivo, in situ tissue comprises heart tissue and the organ dysfunction comprises at least one of cardiac dysfunction or cardiac arrest.

19. A method of monitoring a patient, the method comprising:
    illuminating in vivo, in situ tissue of the patient with an excitation beam at a wavelength of 441 nanometers;
    collecting Raman-shifted light scattered from the in vivo, in situ tissue of the patient in response to the excitation beam;
    determining a spectrum of the Raman-shifted light;
    determining relative concentrations of each of plurality of chromophores in the in vivo, in situ tissue based on the spectrum of the Raman-shifted light and a library of Raman spectra from whole mitochondria in reduced and oxidized states, the library of Raman spectra representing weighted average redox states of cytochromes in the whole mitochondria and effects of the cytochromes on each other in a mitochondrial membrane of the whole mitochondria;
    determining, based on the relative concentrations, at least one of a redox state of whole mitochondria, hemoglobin oxygen saturation, myoglobin oxygen saturation, or redox state of individual cytochrome complexes in mitochondria of the in vivo, in situ tissue; and
    determining and/or predicting a dysfunction of the in vivo, in situ tissue based on the the redox state of whole mitochondria, hemoglobin oxygen saturation, myoglobin oxygen saturation, or redox state of individual cytochrome complexes in mitochondria of the in vivo, in situ tissue.

20. The method of claim 19, wherein illuminating the in vivo, in situ tissue occurs during surgery, and further comprising:
    determining adequacy of tissue protection during surgery based on the at least one of the redox state of whole mitochondria, hemoglobin oxygen saturation, myoglobin oxygen saturation, or redox state of individual cytochrome complexes in mitochondria of the in vivo, in situ tissue.

21. The method of claim 19, wherein determining the relative concentrations of each of the plurality of chromophores comprises:
    determining an estimate of weighted spectra to a spectrum of the Raman-shifted light; and
    iteratively adjusting the estimate of weighted spectra; and determining the relative concentrations based on the estimate of weighted spectra.

22. The method of claim 19, further comprising:
    predicting tissue function following reperfusion of the in vivo, in situ tissue based on the at least one of the redox state of whole mitochondria, hemoglobin oxygen saturation, myoglobin oxygen saturation, or redox state of individual cytochrome complexes in mitochondria of the in vivo, in situ tissue.

* * * * *